United States Patent [19]
Evans

[11] Patent Number: 5,181,416
[45] Date of Patent: Jan. 26, 1993

[54] APPARATUS AND METHOD FOR TESTING POINT SHARPNESS OF NEEDLES

[75] Inventor: Alfred G. Evans, Torrington, Conn.

[73] Assignee: United States Surgical Corporation, Norwalk, Conn.

[21] Appl. No.: 541,055

[22] Filed: Jun. 20, 1990

[51] Int. Cl.$^5$ ............................................. G01N 3/58
[52] U.S. Cl. .................................................. 73/104
[58] Field of Search ................... 73/104, 81, 82, 83, 73/84, 85, 78, 865.9

[56] References Cited

U.S. PATENT DOCUMENTS

| | | | |
|---|---|---|---|
| 2,740,296 | 4/1956 | Andres | 73/104 X |
| 3,418,855 | 12/1968 | Apat | 73/104 X |
| 3,817,090 | 6/1974 | Michel | 73/81 |
| 3,902,358 | 9/1975 | Moore | 73/104 |
| 3,955,407 | 5/1976 | Rozett | 73/769 X |
| 3,956,924 | 5/1976 | Hansen et al. | 73/81 |
| 4,094,188 | 6/1978 | Bellouin et al. | 73/81 |
| 4,160,325 | 7/1979 | DeNicola | 33/788 |
| 4,194,402 | 3/1980 | DeNicola | 73/859 |
| 4,302,967 | 12/1981 | Dufey | 73/84 |
| 4,721,000 | 1/1988 | Scanlon | 73/833 |
| 4,951,512 | 8/1990 | Mazza et al. | 73/864.23 |
| 5,000,912 | 3/1991 | Bendel et al. | 420/34 |
| 5,022,273 | 6/1991 | Evans | 73/849 |

FOREIGN PATENT DOCUMENTS

| | | | |
|---|---|---|---|
| 0294210 | 12/1988 | European Pat. Off. | |
| 715934 | 2/1980 | U.S.S.R. | 73/104 |
| 1298510 | 3/1987 | U.S.S.R. | 73/104 |
| 1456111 | 2/1989 | U.S.S.R. | |
| 1499208 | 1/1978 | United Kingdom | 73/104 |

OTHER PUBLICATIONS

"Biomechanics of Curved Surgical Needle Bending", Journal of Biomedical Research, vol. 23, No. A1, pp. 129-143, 1989, Michael R. Abidin et al.

"A New Quantitative Measurement for Surgical Needle Ductility", Annals of Emergency Medicine, vol. 18, pp. 64-68, Jan. 1989, Michael R. Abidin et al.

"Operator's Manual for Curved Needle Fixture", designated Manual #M10-CR5368-1, published by Instron Corporation, Canton, Mass., pp. 1-2, published by Dec. 1991.

"New Developments in Hypodermic Needles"; Brian E. Baldwin, Bulletin of the Parenteral Drug Association; Nov.-Dec. 1971, vol. 25, No. 6, pp. 270-278.

"Purchasing Digest/Needle Sharpness Testing", N. J. Menolasino et al. 2 pages published by Nov. 1988.

Primary Examiner—Tom Noland
Attorney, Agent, or Firm—Thomas R. Bremer; Peter G. Dilworth; Rocco S. Barrese

[57] ABSTRACT

An apparatus and method to determine the sharpness of a curved surgical needle point by a measurement of the perpendicular forces required to push the needle point through a supported membrane at a given rate of penetration. The apparatus includes a needle penetration fixture having a needle penetrable membrane, a load cell, and related control and recordation instrumentation. According to the method a needle is mounted on a rotatable fixture and first precisely aligned. Thereafter, the fixture is rotated so as to cause the needle to penetrate the membrane whereby the force necessary to penetrate the membrane force being recorded by recordation instrumentation and the process being controlled by control instrumentation.

19 Claims, 8 Drawing Sheets

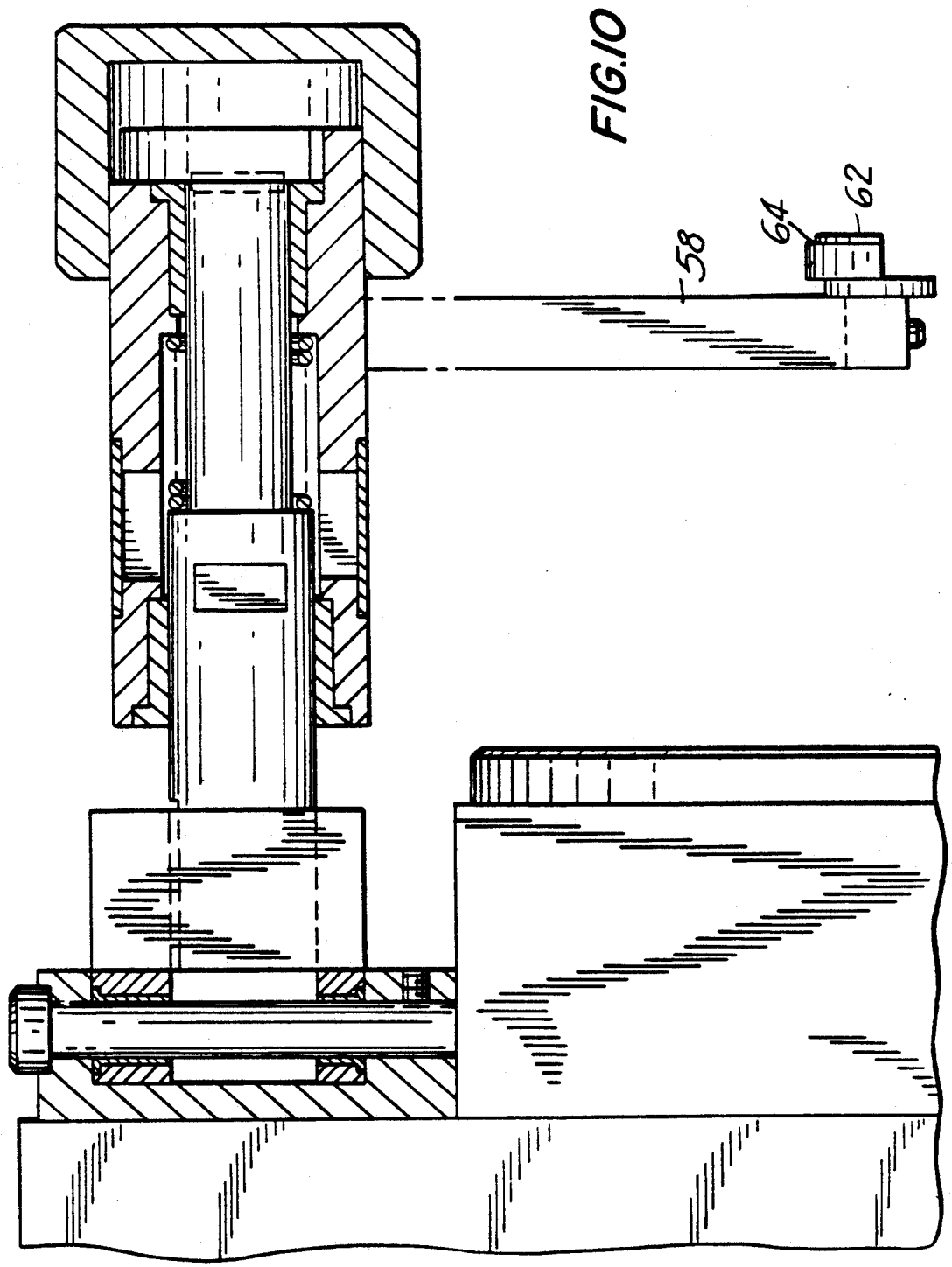

APPARATUS AND METHOD FOR TESTING POINT SHARPNESS OF NEEDLES

BACKGROUND OF THE INVENTION

1. Field of the Invention

The present invention relates to testing the sharpness of needles. In particular, the invention relates to an apparatus and method to determine the sharpness of the point of a curved surgical needle by measurement of the forces required to push the needle point through a supported membrane.

2. Description of Related Art

A point may be defined as a microscopic area forming the connecting surface to three or more macroscopic planes These planes intersect at a solid interior angle of less than 180°. As the angle of intersection or as the radius of the tip of the point decreases, the tip becomes sharper and requires less force to penetrate an object or surface.

Various refinements have been made over the years in the structures of surgical needles. It is considered advantageous in the field to structure sharpness characteristics of surgical needles toward the purpose of achieving the most efficient penetrating function. This goal facilitates ease of use by the surgeon and minimizes pain and apprehension of the patient. Regardless of the innovation in structure, uniformity in the sharpness of surgical needles has been difficult to achieve. High volumes of surgical needles are used each year. Since they are mass produced, selected samples must be subjected to testing procedures.

Among known methods for determining the sharpness of a point is visual examination under a microscope. Physical examination or noting contour by touch has also been used. Major drawbacks of such testing are the lack of uniformity and reproducibility of the test results.

Needle test apparatus which are automatic in operation have been devised. However, such systems which often utilize complicated electrical and mechanical components are subject to certain drawbacks. Beside their complexity they are generally bulky and their size limits their adaptation to portable usage.

There exist pocket sized point sharpness testers which measure depth to width ratio of a test point. One drawback of these devices is that they warn the user if the sharpness of a point is greater than a predetermined ratio, but they do not produce an absolute measure. Because of this drawback, such devices have not been greatly used for testing surgical needles. Furthermore, since sharpness or dullness is being determined by geometric configuration alone, it is necessary that the point have sufficient strength and rigidity to maintain its original shape when touched.

Another method of testing the sharpness of needles involves measuring the linear displacement of a resilient support.

A major disadvantage of devices for testing curved needles is that the curvature of the needle renders it difficult to pierce a test bed with the needle in a manner that perpendicularity of the needle with respect to the test bed is maintained at all times during the test. For example, even a slight variation of the movement of the needle from the true radius thereof will cause the needle to penetrate the test bed by forces other than pure piercing forces, i.e., forces caused by movement of the body of the needle in the plane of the test bed.

To date, an apparatus and method for quantitatively and accurately testing the point sharpness of needles which utilizes a measure of perpendicular force required to push a needle point through a supported membrane at a given rate of penetration, have not yet been devised. I have invented an apparatus and method which accomplish this objective.

SUMMARY OF THE INVENTION

The invention relates to an apparatus for determining the sharpness of the point of a needle which comprises means to measure force in a predetermined direction, means connected to the force measuring means and penetrable by the point of a needle to be tested, means to grip the needle to be tested, means to align the needle adjacent the needle penetrable testing means at a preselected location and orientation to permit the needle to penetrate the penetrable testing means in a predetermined direction and orientation with respect to the penetrable testing means, means to cause the needle to penetrate the penetrable testing means, and means to determine the force exerted by the needle on the needle penetrable testing means. Preferably, the force measuring means is a load cell and the needle penetrable testing means is a membrane material penetrable by the needle being tested. The means to grip the needle is preferably a needle clamp adapted to clamp a needle of arcuate configuration. The means to align the needle adjacent the needle penetrable membrane is preferably a radius segment connected to an extension member pivotal to and away from a position adjacent the needle test location so as to permit alignment of the needle with respect to the needle gripping means, while being pivotably movable to a position distal from the test location.

In a preferred embodiment, the needle penetrable testing means is a sheet of plastic material maintained in stretched condition across a membrane holding means. The membrane holding means has a generally circular cross-sectional configuration and comprises means to support the membrane on the side opposite the needle penetration side. The supporting means further comprises a plurality of apertures which are located to permit penetration of the membrane by the needle while portions of the membrane supporting means defining the apertures support the membrane during penetration by the needle. In the application contemplated, the test needle is a circular surgical needle and the needle holding means is structured to support the needle in a manner to rotate the needle about the center of the circle defined by the needle, while the point of rotation is approximately coincident with the penetrated surface of the membrane. For such needles, the sheet of plastic material is preferably Scotchpak brand plastic material.

In the preferred embodiment an apparatus is disclosed to determine the sharpness of a point of a needle of circular configuration by a measurement of the maximum perpendicular force required to cause the needle point to penetrate a needle penetrable supported membrane at a predetermined rate of penetration, which comprises a membrane of plastic sheet material capable of being penetrated by the needle, a needle penetration fixture comprising means to support the membrane, means to secure the membrane in a taut condition on the membrane support means, means to releasably grip a needle at one end portion and positioned at a location adjacent the membrane and capable of gripping the needle in such manner that the needle point is perpendicular to the membrane when the needle is caused to penetrate the membrane. Means to align the needle with respect to the membrane is provided such that the center of the circle defined by the needle is substantially coincident with the upper surface of the membrane and is located such that rotation of the needle will cause penetration of the membrane in a predetermined area of the membrane. Means is provided to rotate the needle gripping means and the needle therewith in a manner which maintains the center of rotation of the needle within a predetermined range, whereby the needle is rotated toward the membrane and is caused to penetrate the membrane, and continued rotation of the needle gripping support means causes continued rotation of the needle with the predetermined dimensional range being maintained such that the needle point is substantially normal to the membrane during the rotational motion. The invention further comprises means electrically connected to the penetration fixture and capable of providing signal means arranged to provide a signal in dependence on the force of the needle as the needle penetrates the membrane. The signal providing means is a load cell and means is provided to control the load cell.

The apparatus further comprises means to determine the perpendicular force based upon the signal provided by the signal means. Further, the means to control the load cell and the means to determine the perpendicular force on the membrane includes instrumentation comprising a computer having compatible load cell software, a controller, and a motor drive.

The load cell is an Instron Brand Model 1123 or any equivalent 2000 gram load cell, and the membrane is a sheet of Scotchpak brand 1220 membrane approximately 0.0002 inch thickness. Preferably, the computer is an IBM brand PC AT or an equivalent computer, and the software is an Instron Brand Series IX software. The controller is a DAEDAL brand MC 2000 controller, and the motor drive is a DAEDAL brand MD series drive.

A method is also disclosed for determining the sharpness of the point of a needle which comprises providing means to measure force in a predetermined direction, providing means connected to the force measuring means and penetrable by the point of a needle to be tested, gripping the needle to be tested, aligning the needle adjacent the needle penetrable means at a preselected location and orientation so as to permit the needle to penetrate the penetrable testing means in a predetermined direction and orientation with respect to the penetrable means, causing the needle to penetrate the penetrable means, and determining the force exerted by the needle on the needle penetrable means.

BRIEF DESCRIPTION OF THE DRAWINGS

Preferred embodiments of the invention are described hereinbelow with reference to the drawings wherein:

FIG. 10 is a cross-sectional view taken along lines 10—10 of FIG. 9, illustrating a side view of the radius block utilized for alignment of the needle.

DETAILED DESCRIPTION OF THE PREFERRED EMBODIMENTS

Figure 1:
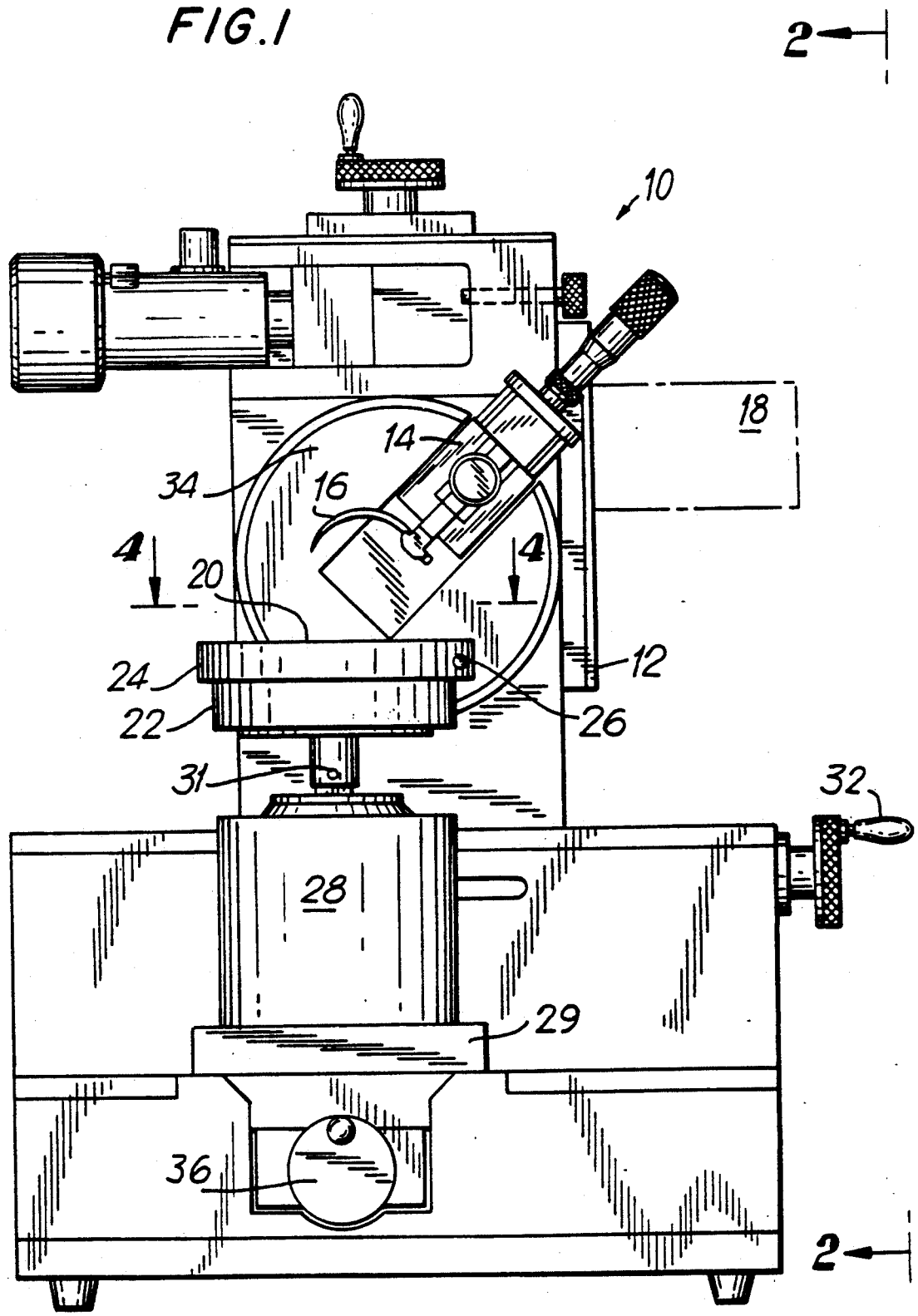
FIG. 1 is a front elevational view of a needle penetration fixture constructed according to the present invention.
Figure 2:
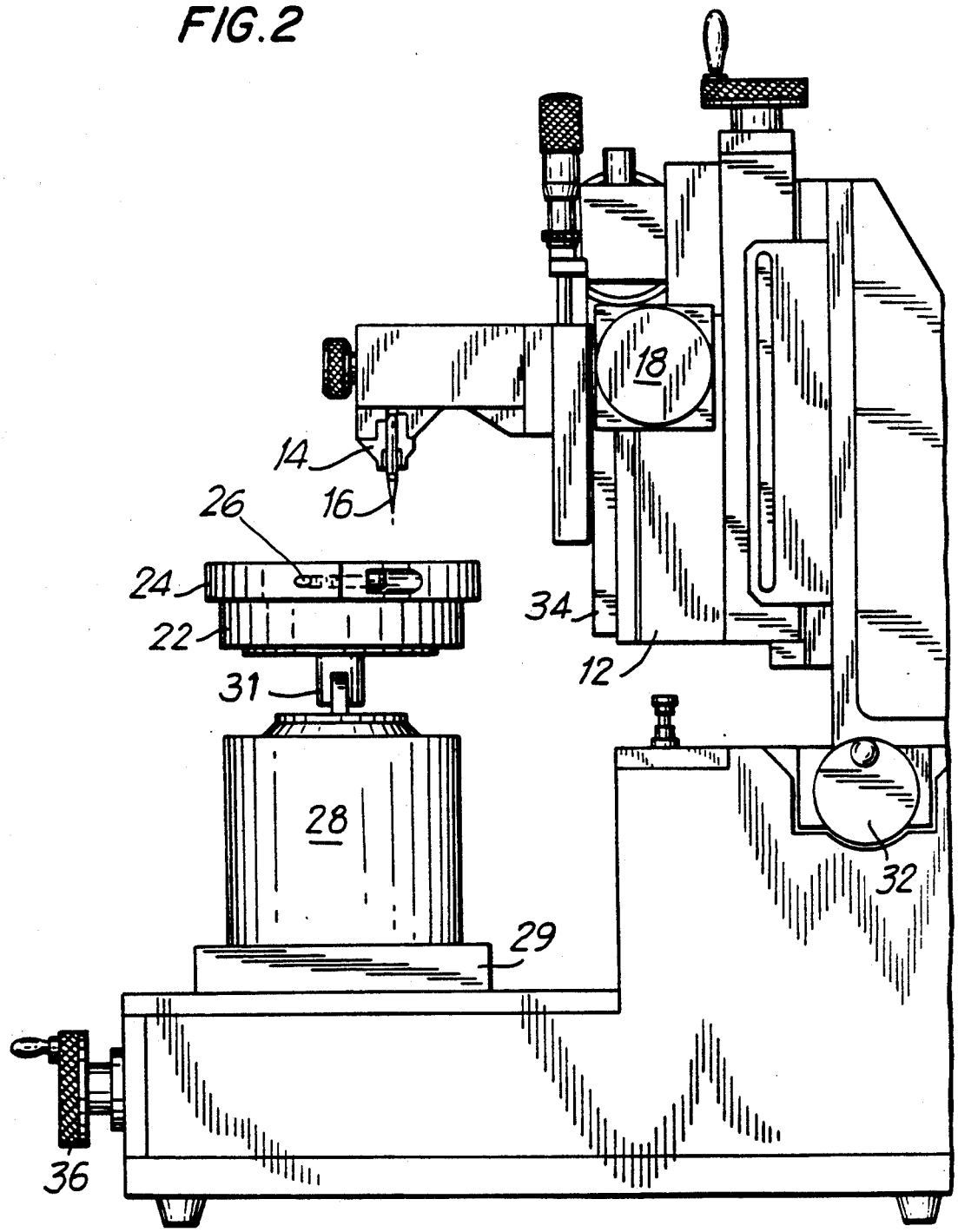
FIG. 2 is a side view of the needle penetration fixture taken along lines 2—2 of FIG. 1, illustrating the membrane fixture in cross-section.
Figure 3:
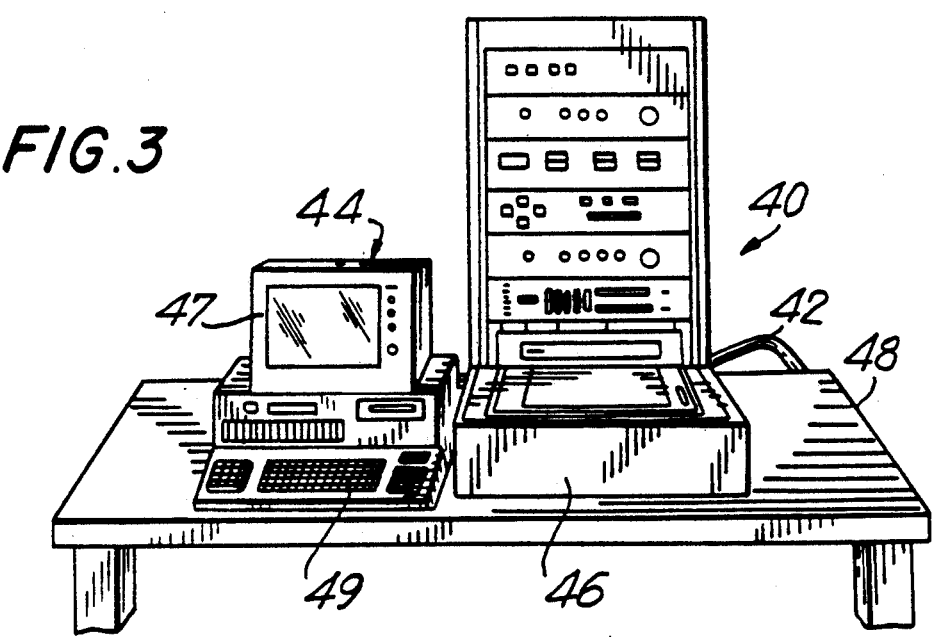
FIG. 3 is a frontal view from above of the equipment for reception and recording of data generated by the apparatus of FIG. 1.

An apparatus according to the present invention is used to determine the sharpness of a curved surgical needle point by a measure of the perpendicular forces required to penetrate or puncture a supported membrane. The sharpness of a curved surgical needle is evaluated by penetration testing. The testing apparatus includes a penetration fixture as shown in FIGS. 1 and 2, a load cell, and a membrane. Control and recordation instrumentation are shown in FIG. 3.

Figure 4:
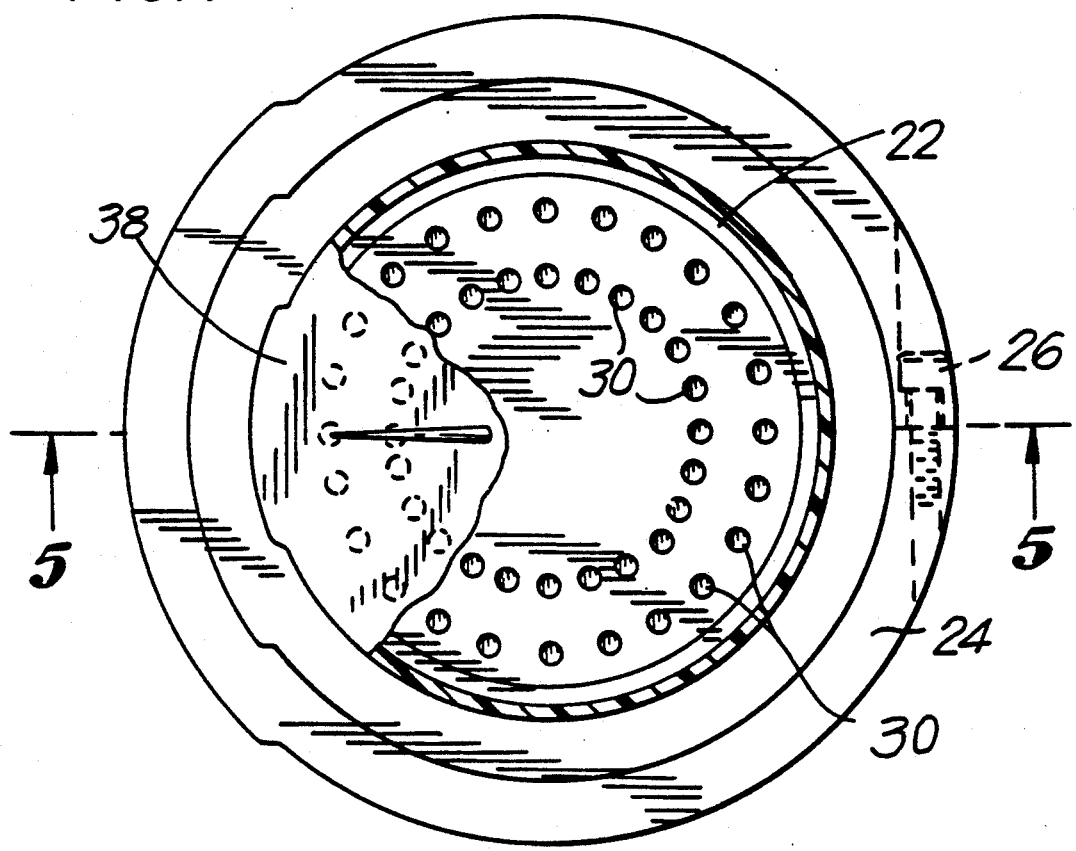
FIG. 4 is a view taken along lines 4—4 of FIG. 1, of the membrane holding fixture, illustrating a needle in position for testing sharpness by penetration of the membrane.
Figure 5:
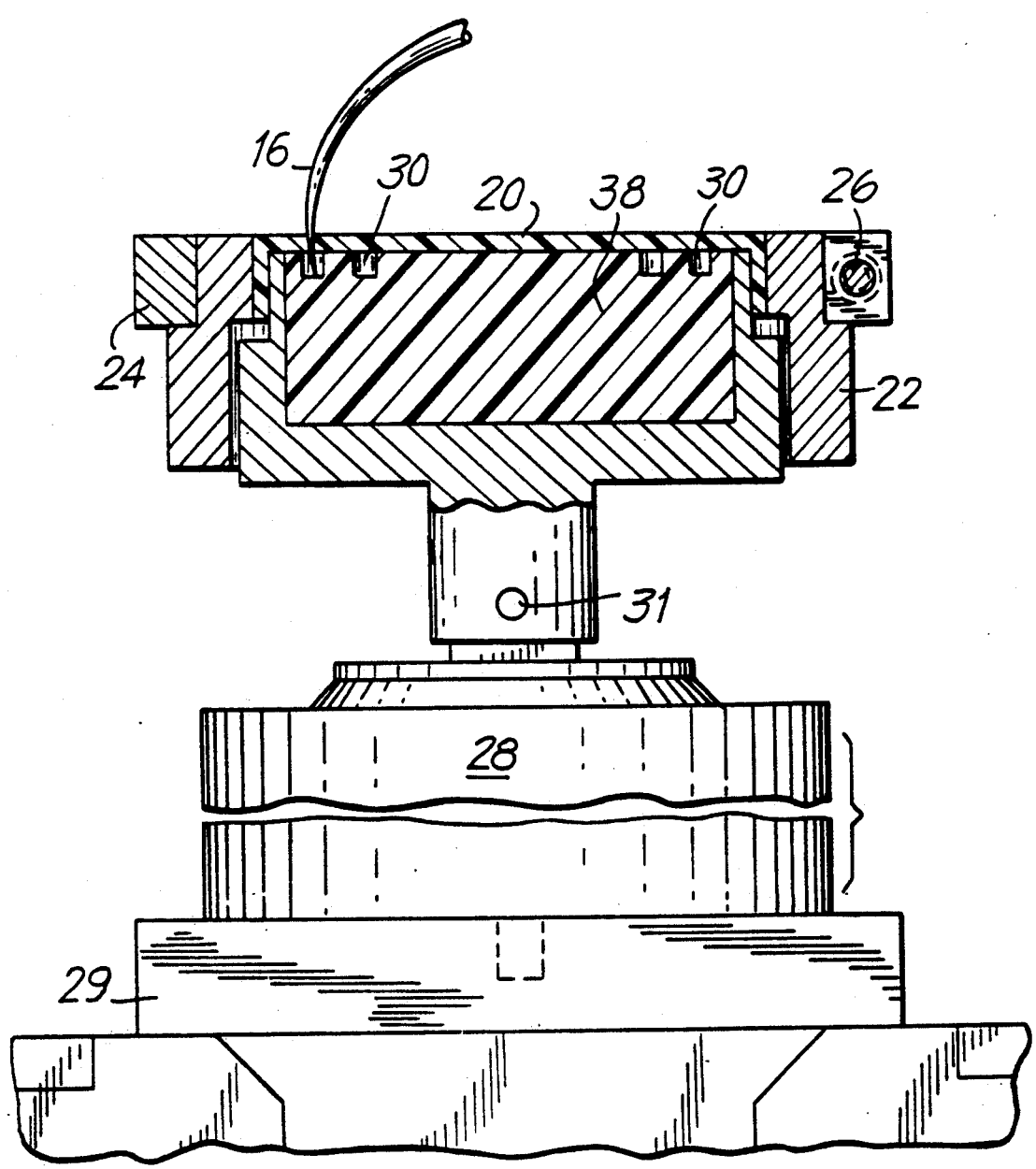
FIG. 5 is a cross-sectional view taken along lines 5—5 of FIG. 4, illustrating the testing membrane being pierced by a needle under test conditions.

Referring initially to FIGS. 1, 2 and 5, the penetration fixture 10 constructed according to the present invention is illustrated. The fixture 10 includes a frame 12 having rotatable clamp assembly 14 which holds needle 16 and is arranged to rotate by rotating table drive motor 18 shown in FIG. 2. Membrane holder 22 includes membrane ring 24 which secures membrane 20 tightly across the upper portion of the holder and is tightened by screw 26. Membrane holder assembly 22 is attached to load cell 28 at pin 31. The load cell 28 is arranged to measure downward forces exerted on the membrane by a needle under test. A membrane support block 38 constructed of a lightweight plastic material such as nylon, is shown in FIGS. 4 and 5. The support block contains two circular patterns of apertures 30 as shown in FIG. 4. Block 38 supports the membrane 20 while permitting penetration of a test needle into the membrane at each location of an aperture 30.

Needle clamp assembly 14 is attached to rotary table 34 and is rotated by drive motor 18, which is preferably of the stepper motor type, for rotating the needle clamp assembly 14 along with needle 16. Load cell 28 is secured to adjustable table 29 and to membrane holder assembly 22 as shown in FIGS. 1 and 2.

Referring to FIG. 1, a side-to-side adjustment crank 32 is suitably connected by mechanical linkage (e.g. rack and pinion, not shown) to adjust the side-to-side position of the rotatable table 34 and consequently of needle holder 14 therewith. A front to rear adjustment mechanism is provided to permit adjustment of the position of table 29, front to rear, by crank 36 which is also suitably connected to a mechanical adjustment device, preferably a rack and pinion arrangement.

Referring now to FIG. 3, electronic equipment 40 is arranged to receive data provided by load cell 28 via connecting line 42 for display at terminal base 44 on monitor 47, and printed on printer 46, all supported on table support 48.

Referring to FIG. 4 in conjunction with FIGS. 1 and 2, the membrane securement bolt 26 is shown from above. A membrane 20 is stretched across holder 22 and secured tightly by ring 24 with support block 38 positioned beneath the membrane so that apertures 30 in block 38 expose selected portions of the membrane as shown and permit penetration of the membrane at those locations over the apertures. The membrane 20 is preferably in the form of a plastic material such as Scotchpak brand plastic film, 0.002 inch thickness. Other films readily penetratable by needles being tested. Preferably, the load cell 20 is an Instron Model 1123 having capability of up to 2000 grams. Other load cells similar to the Instron 1123 are also contemplated.

As noted, the block 38 defines a plurality of circular apertures 30 which expose selected portions of the taut membrane for penetration by a needle under testing procedures. Block 38 may be in the form of a plate which defines apertures as shown.

In operation, once ring 24 is positioned to secure membrane 20 and the membrane is securely tightened, it is necessary to mount the needle in the needle holder and to position the needle such that rotation of the needle holder takes place about the true center of the circle defined by the needle. This procedure insures perpendicularity between each portion of the needle and the membrane as penetration takes place.

Figure 7:
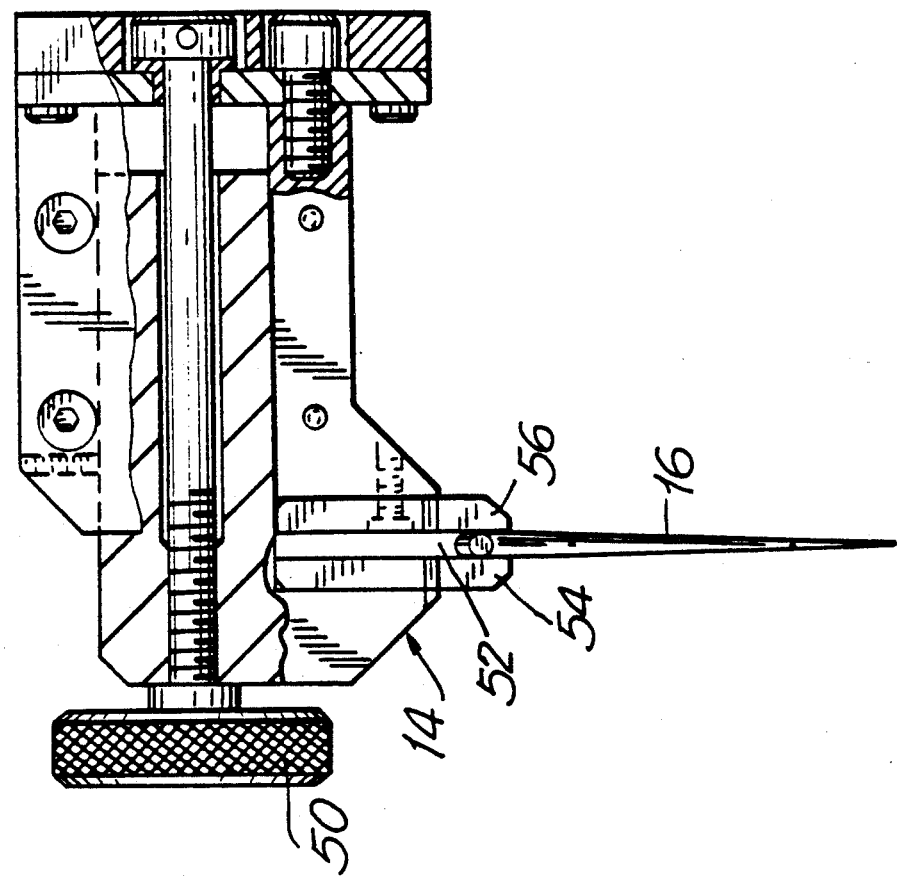
FIG. 7 is a side view of the fixture shown in FIG. 6, illustrating the needle positioned in the needle holding fixture.
Figure 6:
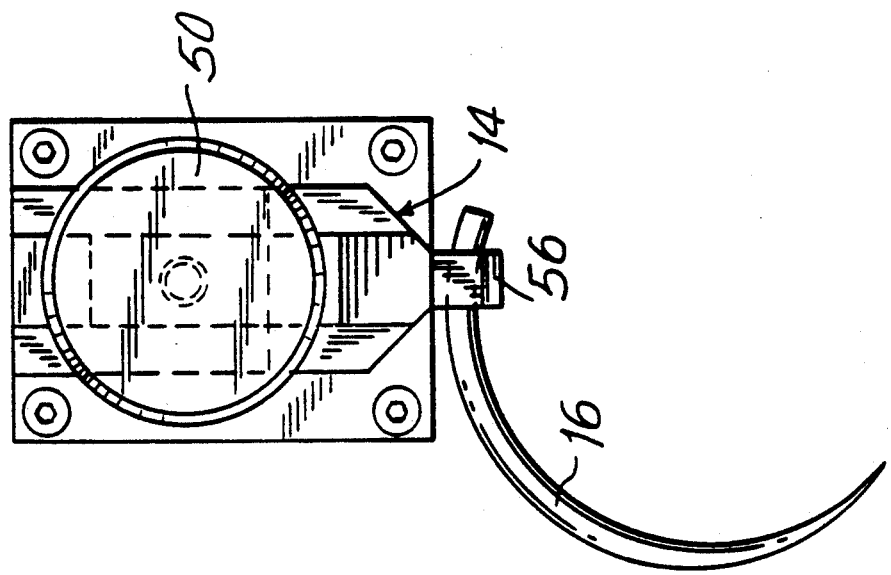
FIG. 6 is an enlarged view of the needle holding fixture.
Figure 8:
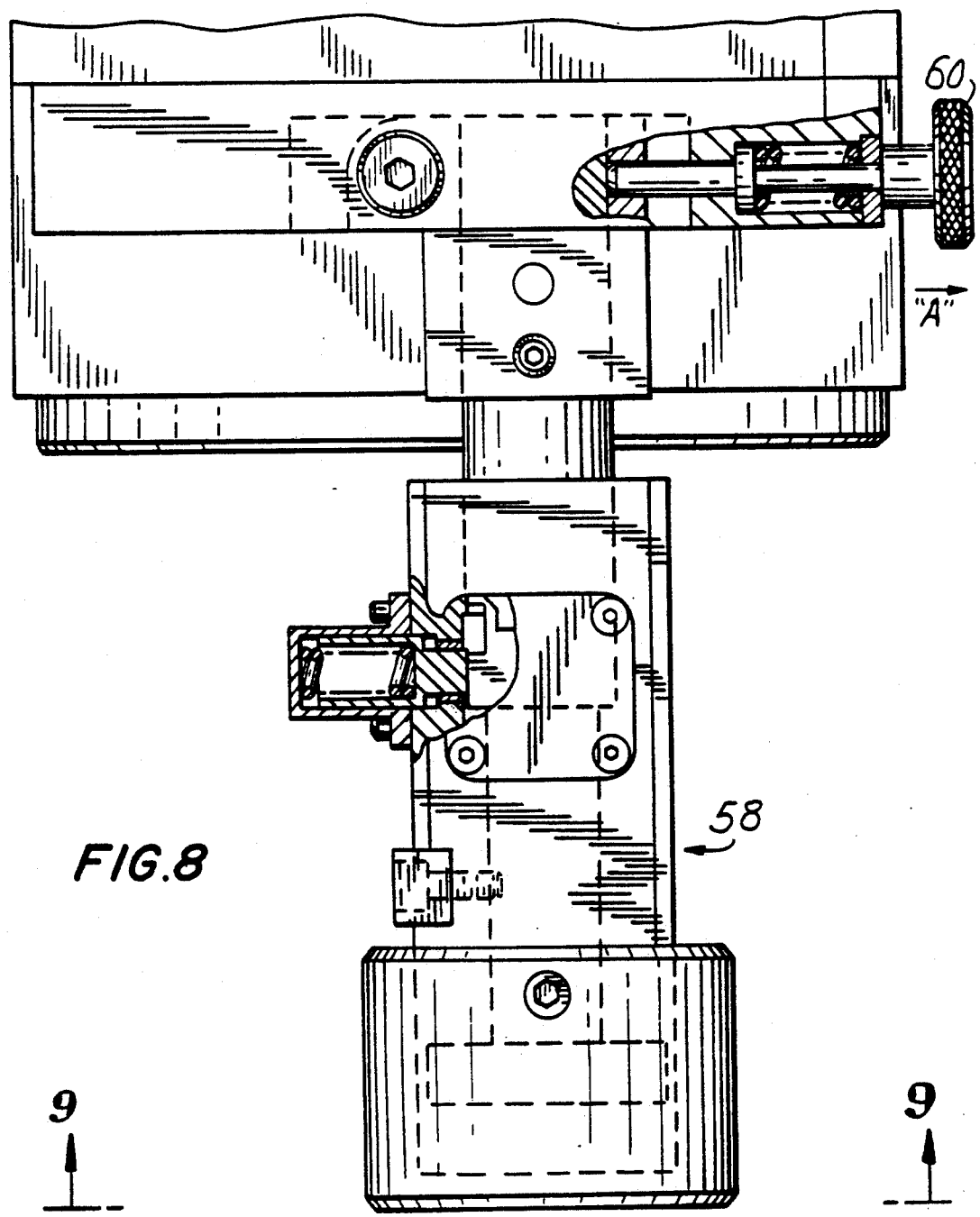
FIG. 8 is a top view, partially cut away, of the apparatus of FIG. 1.
Figure 9:
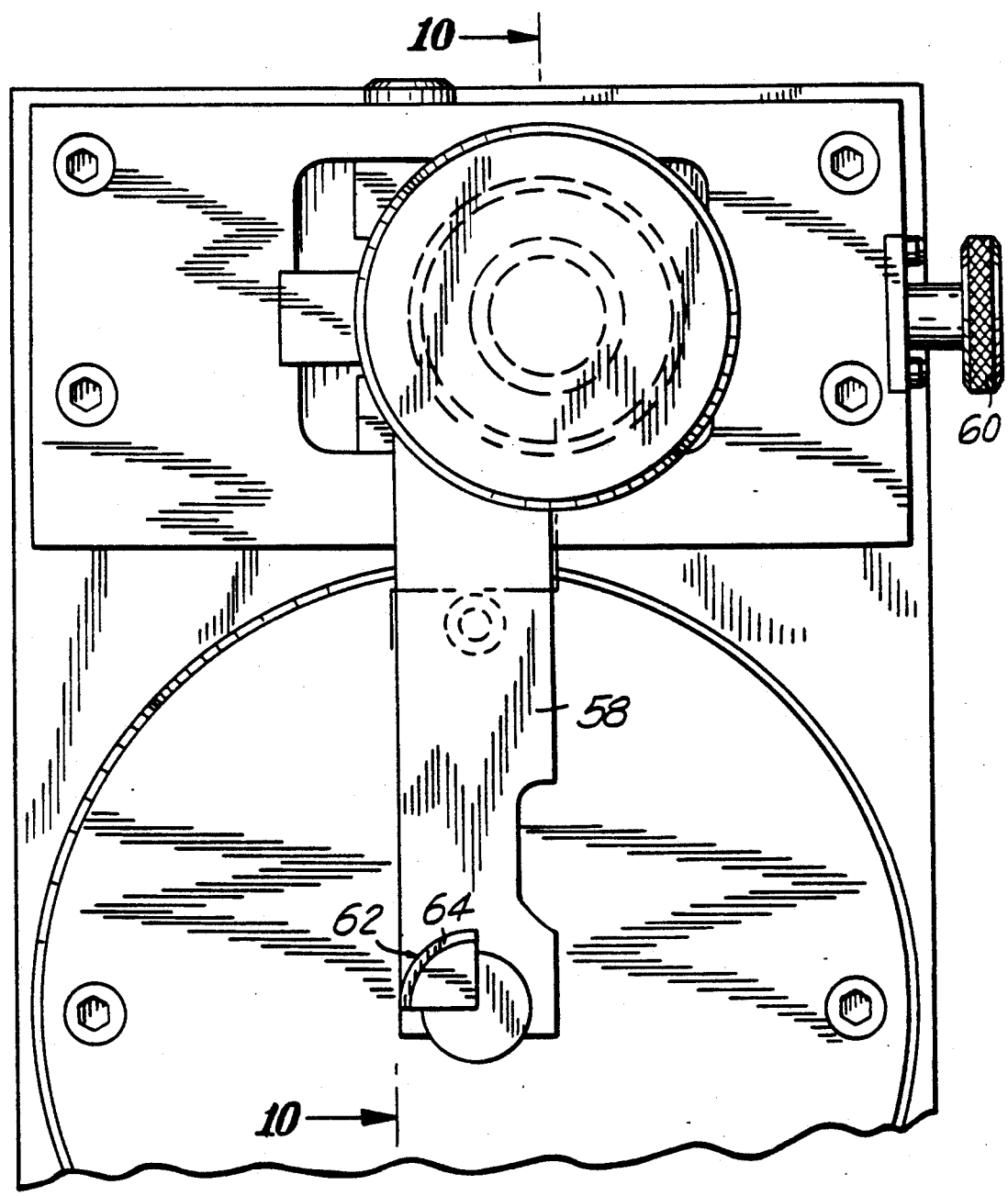
FIG. 9 is a view taken along lines 9—9 of FIG. 8, illustrating the radius block arrangement utilized for correctly aligning a curved needle to be tested.

Referring now to FIGS. 6 and 7 in conjunction with FIGS. 1 and 2, needle holder 14 is shown with knurled adjustment ring 50 used to adjust the gap 52 between plates 54, 56 in which needle 16 is gripped. Once needle 16 is gripped within gap 52 as shown in FIGS. 6 and 7, it is necessary to align the needle with a circular opening 30 which exposes membrane 20. Side-to-side and fore and aft positioning of the membrane is accomplished by adjustment cranks 36 and 32 followed by securely locking the position of the load cell and membrane. Thereafter, pivotal arm 58 is released by pulling spring loaded knurled knob 60 outwardly as shown by arrow "A" in FIG. 8, such that arm 62 is pivoted downwardly approximately 90 degrees toward the membrane as shown in FIG. 9. Thus, radius segment 62 (FIG. 9) is now positioned where needle 16 is to be mounted to holder 14. Radius segment 62 includes a circumferential step 64 shown more clearly in FIG. 10, for temporary reception of arcuate needle 16. The radius of the segment 62 along the step 64 is identical to that of needle 16. At this time the needle holder 14 is positioned adjacent the radius segment 62. Positions of both the needle holder and radius segment are then adjusted to align the center of the segment and the center of the needle such that they just touch the central portion of the exposed membrane over an aperture 30 selected for testing the needle. At this time, the needle is positioned within gap 54 of the holder 14 while the center of the arc defining the needle is coincident with the upper surface of the membrane.

The test thereafter proceeds by actuating stepper motor 20 to cause rotatable table 34 to rotate with needle 16 to penetrate membrane 20, with the needle being precisely perpendicular to the plane of the membrane during the entire motion of the needle. As noted, this preciseness of dimension and location prevents lateral motion of the needle into the membrane and provides an accurate measure of downward forces on the membrane at all times.

The downward force of the needle penetrating the membrane will vary in dependence upon the sharpness of the needle. Thus, the sharper the needle, the lower the critical force on the membrane. This force is transmitted to the load cell 28 which in turn generates a transmissible signal to the electronic processing center with the display on computer monitor 44 or optional printout on plotter 46. In practice the force will be greatest just prior to penetration and will then be reduced after penetration of the membrane proceeds. The data can then be collected and analyzed. In a given test for a needle, several penetrations can be accomplished with one needle by simply readjusting the position of the membrane by rotating the membrane holder 22 to successively align circular apertures under the needle holder and repeating the above described procedure to test the needle. Alternatively, several needles can be tested with a single membrane. In either case, the point of rotation of the needle is relatively precisely fixed such that at all times the perpendicularity between the arcuate needle and the membrane is maintained.

As noted, the membrane 20 used for the testing procedure is a sheet of thin material. The membrane must be penetrable by the needle. As noted, a thin laminated synthetic membrane such as Scotchpak brand film 1220 which is approximately 0.002 inches thick is preferred.

Referring to FIG. 3 in the preferred embodiment, the control and recordation instrumentation includes:

a) An IBM AT brand personal computer 44 or an equivalent computer loaded with software compatible with the load cell, e.g., Instron Brand Series IX Software.

b) A controller, e.g., DAEDAL brand MC 2000 controller.

c) A motor drive, e.g., DAEDAL brand MD series drive.

The control and recordation instrumentation is electronically connected to the penetration fixture. The instrumentation of the load cell includes sensing means to detect the amount of force on the membrane. This data is transmitted to the computer 44 and a chart of loads is generated by a plotter 46. The operator can read the chart to note the maximum perpendicular force on the membrane.

Referring again to FIG. 1, FIG. 2 and FIG. 5, the method for testing needles on the apparatus of the invention includes aligning the curved surgical needle in position utilizing the pivotal arm 58 and radius segment 62. Once the correct alignment and position of the needle is obtained the needle is mounted in the gripping clamp 14 which will fix the needle with the point precisely perpendicular to the upper surface of the membrane. During operation, when the needle is rotated into the membrane, the needle is forced through the membrane. The maximum amount of vertical force is logged by the control and recordation instrumentation of FIG. 5. As noted, sharper needles will have a lower maximum force for a given needle point geometry, and wire size. Needles of less sharpness will generate a greater maximum force.

The load cell 28 is placed into the penetration fixture and is connected to the Instron ® Universal Testing Machine. Various adjustments on the apparatus are performed e.g., balance and calibration of the load cell 21, selection of the full scale load, adjustment of the balance dial, etc. During the testing set-up phase the operator must make certain that there is ample space on the travel of crosshead 68 to avoid interference between the radius segment and the needle holder. It is important that the needle not contact any surface that may dull or damage the point since the sharpness of the point is to be evaluated.

After the testing set-up phase, the recordation and control instrumentation is initialized. The operator can first set up the computer 44 for the testing procedure. The power to the computer and its components e.g., monitor 47 and plotter 46 is turned on. The user will input to the computer through a keyboard 49, the necessary information to perform the test. Some of the pertinent information includes: test type which in this case is compressive; needle type; membrane type; penetration fixture type; crosshead speed; geometry of the needle e.g., cylindrical.

The operator will next initialize the controller. Once the power is on the necessary parameters may be set. Among these parameters are: preset travel, preset velocity, and acceleration.

The testing procedure can then begin. It should be verified that the compression load cell 12 is properly connected onto the fixture. To install the membrane, circular section of the membrane material is cut, preferably with about a four inch diameter. The membrane is placed on the support holder 22. If a Scotchpak brand membrane of 0.002 inch thickness is used, the shiny side should face up on the membrane support holder 22. The membrane is secured on the support disc 22 by pushing the membrane ring 24 down to its lowest position over the membrane and securing screw 26. To ensure accurate test results, the operator must be sure there is sufficient tension on the membrane to keep the membrane from tenting (i.e. assuming a non-planar configuration) more than 0.5 inches during the needle penetration. The membrane must be maintained in a stretched condition.

The operator must determine the average profile radius of the curved surgical needle being tested to the nearest 0.001 inch. The user will select a locating arbor or recess that is calibrated to within ±0.001 inch of the average profile radius of the curved needle being tested. The correct needle locating radius segment 62 is installed in the locating arm 60. Radius segments must vary in dimension corresponding to the radius of curvature of the needle being tested. It is important to establish the profile radius of the needle and to select the proper locating radius segment because the needle must penetrate the membrane at a 90° angle at all times during the testing procedure in order to provide an accurate measurement of the perpendicular force.

The locating arm 58 is then returned to the test position and the needle is placed into the needle holder 14. Thereafter, the needle clamp jaws 54, 56 are tightened around approximately the rear one-third portion of the needle, i.e. the stem.

The membrane 20 and needle 16 are adjusted appropriately so that the needle has sufficient clearance for ninety degrees of penetration. The load cell 12 is rebalanced from the control panel (shown in FIG. 5).

The actual testing may now be performed. The user will depress the appropriate button on the controller to activate motor 18 causing the needle holder 14 and test needle to penetrate the membrane. The needle will rotate downwardly toward the membrane at a constant rate. The force on the membrane is recorded by the control and recordation instrumentation.

A feature of the present invention resides in the fact that the needle support will rotate with the needle with the center of rotation being maintained in a predetermined range such that the needle will penetrate the membrane at a substantially perpendicular angle relative thereto.

The recordation instrumentation generates a permanent copy of the perpendicular force required to push the needle point through the supported membrane. The operator can reset the apparatus and test other needles by rotating and resetting the membrane as described.

I claim:

1. An apparatus for determining the sharpness of the point of a needle of substantially circular configuration which comprises:
   means to measure force in a predetermined direction;
   needle penetrable means connected to said force measuring means and penetrable by the point of the needle to be tested;
   means to grip the needle to be tested in a manner for rotation;
   means to selectively align the needle adjacent said needle penetrable testing means, said alignment means comprising a substantially circular radius segment supported by a member so that said radius segment is movable to and away from a position adjacent the needle test location so as to permit alignment of the needle with respect to said needle grip means such that the center of the needle is substantially coincident with the upper surface of said needle penetrable means at a preselected location and orientation to permit the needle to penetrate said needle penetrable means at a predetermined location and in the predetermined direction and orientation with respect to said needle penetrable means;
   means to cause the needle to rotate so as to penetrate said needle penetrable means; and
   means to determine the force exerted by the needle on said needle penetrable means.

2. The apparatus according to claim 1 wherein said force measuring means is a load cell.

3. The apparatus according to claim 2 wherein said needle penetrable means is a membrane material penetrable by the needle being tested.

4. The apparatus according to claim 3 wherein said means to grip the needle is a needle clamp.

5. An apparatus for determining the sharpness of the point of a surgical needle of circular configuration which comprises:
   a load cell to measure force in a predetermined direction;
   a needle penetrable membrane connected to said load cell and penetrable by the point of the needle to be tested;
   a needle clamp to grip the needle to be tested;
   means to align the needle adjacent said needle penetrable membrane at a preselected location and orientation to permit the needle to penetrate the needle penetrable membrane in the predetermined direction and orientation with respect to said needle penetrable membrane, the alignment means comprising a radius segment connected to an extension member pivotal to and away from a position adjacent the needle test location so as to permit alignment of the needle with respect to said needle clamp;
   means to cause the needle to penetrate said needle penetrable membrane; and
   means to determining the force exerted by the needle on said needle penetrable membrane.

6. The apparatus according to claim 5 wherein said needle penetrable membrane is a sheet of plastic material maintained in stretched condition across a membrane holding means.

7. The apparatus according to claim 6 wherein said membrane holding means has a generally circular cross-sectional configuration.

8. The apparatus according to claim 7 wherein said membrane holding means further comprises means to support said membrane on the side opposite the needle penetration side, said supporting means further comprising a plurality of apertures which are located to permit penetration of said membrane by the needle while portions of said membrane supporting means defining said apertures support said membrane during penetration by the needle.

9. The apparatus according to claim 8 wherein said needle holding means is structured to support the needle in a manner to rotate the needle about the center of the circle defined by the needle, while the point of rotation is approximately coincident with the penetrated surface of said membrane.

10. The apparatus according to claim 9 wherein said sheet of plastic material has a thickness of approximately 0.002 inches.

11. An apparatus to determine the sharpness of a point of a needle of circular configuration by a measurement of the maximum perpendicular force required to cause the needle point to penetrate a needle penetrable supported membrane at a predetermined rate of penetration which comprises:
   a) a membrane of plastic sheet material capable of being penetrated by the needle;
   b) a needle penetration fixture comprising:
      i) means to support said membrane;
      ii) means to secure said membrane in a taut condition on said membrane support means;
      iii) means to releasably grip a needle at one end portion and positioned at a location adjacent said membrane and capable of gripping the needle in such manner that the needle point is perpendicular to said membrane when the needle is caused to penetrate said membrane;
      iv) means to align said needle with respect to said membrane, said alignment means comprising a radius segment supported for movement to and from a position adjacent the needle test location so as to permit alignment of the needle with respect to the needle grip means, such that the center of the circle defined by said needle is substantially coincident with the upper surface of said membrane and is located such that rotation of the needle will cause penetration of said membrane in a predetermined area of said membrane;
      v) means to rotate said needle grip means and said needle therewith in a manner which maintains the center of rotation of said needle within a predetermined range whereby said needle is rotated toward said membrane and is caused to penetrate said membrane, and continued rotation of said needle grip means causes continued rotation of said needle toward said membrane with said predetermined dimensional range being maintained such that said needle point is substantially normal to said membrane during said rotational motion; and
   c) means electrically connected to said penetration fixture and capable of providing signal means in dependence on the force of aid needle as the needle penetrates said membrane.

12. The apparatus according to claim 11 wherein said signal providing means is a load cell.

13. The apparatus according to claim 12 further comprising means to control the load cell.

14. The apparatus according to claim 13 further comprising means to determine the perpendicular force based upon the signal provided by said signal means.

15. The apparatus according to claim 14 wherein said means to control said load cell and said means to determine the perpendicular force on said membrane includes instrumentation comprising:
   a) a computer having compatible load cell software;
   b) a controller; and
   c) a motor drive.

16. The apparatus according to claim 15 wherein said load cell has a load capability of up to 2000 grams.

17. The apparatus according to claim 16 wherein said membrane is approximately 0.002 inches in thickness.

18. The apparatus according to claim 17 wherein said needle is a curved surgical needle.

19. A method for determining the sharpness of the point of a needle of circular configuration which comprises:
   providing means to measure force in a predetermined direction;
   providing means connected to said force measuring means and penetrable by the point of the needle to be tested;
   gripping the needle to be tested;
   aligning the needle adjacent the needle penetrable means at a preselected location and orientation so as to permit the needle to penetrate said penetrable testing means in the predetermined direction and orientation with respect to said penetrable means, said aligning step being facilitated by a radius segment connected to an extension member pivotal to and away from a position adjacent the needle test location so as to permit aligning the needle with respect to the location where the needle is gripped;
   causing the needle to rotate about the center of the circle defined by the needle, while the point of rotation is approximately coincident with the needle penetrable means so as to penetrate said penetrable means; and
   determining the force exerted by the needle on said needle penetrable means.

* * * * *